US010271810B2

(12) United States Patent
Izmirli et al.

(10) Patent No.: US 10,271,810 B2
(45) Date of Patent: Apr. 30, 2019

(54) ENHANCED COMPENSATION OF MOTION IN A MOVING ORGAN USING PROCESSED REFERENCE SENSOR DATA

(71) Applicant: St. Jude Medical International Holding S.á r.l., Luxembourg (LU)

(72) Inventors: Alon Izmirli, Ganot Hadar (IL); Uzi Eichler, Haifa (IL)

(73) Assignee: St. Jude Medical International Holding S.à r. l., Luxembourg (LU)

( * ) Notice: Subject to any disclaimer, the term of this patent is extended or adjusted under 35 U.S.C. 154(b) by 596 days.

(21) Appl. No.: 14/243,254

(22) Filed: Apr. 2, 2014

(65) Prior Publication Data
US 2014/0296657 A1    Oct. 2, 2014

Related U.S. Application Data

(60) Provisional application No. 61/807,511, filed on Apr. 2, 2013.

(51) Int. Cl.
*A61B 5/00* (2006.01)
*A61B 5/02* (2006.01)
(Continued)

(52) U.S. Cl.
CPC .............. *A61B 6/5264* (2013.01); *A61B 5/06* (2013.01); *A61B 5/061* (2013.01); *A61B 5/062* (2013.01);
(Continued)

(58) Field of Classification Search
CPC ......... A61B 5/00; A61B 5/061; A61B 5/1114; A61B 5/721; A61B 6/04; A61B 6/12;
(Continued)

(56) References Cited

U.S. PATENT DOCUMENTS 6,233,476 B1   5/2001   Strommer et al.
7,197,354 B2   3/2007   Sobe
(Continued)

FOREIGN PATENT DOCUMENTS

JP    2007-500565    1/2007
JP    2007-061617    3/2007
(Continued)

OTHER PUBLICATIONS

International Search Report and Written Opinion of the ISA for PCT/US2010/050224 dated Nov. 9, 2010.
(Continued)

*Primary Examiner* — Amanda Lauritzen Moher
(74) *Attorney, Agent, or Firm* — Dykema Gossett PLLC

(57) ABSTRACT

An apparatus includes a positioning system and a patient reference sensor (PRS). The positioning system acquires a plurality of raw PRS readings over time, which can indicate the position and orientation of the PRS. A filter is configured to process the raw PRS readings and output filtered PRS readings. The filter outputs filtered PRS readings as a baseline value while the raw PRS readings stay within a predetermined range and output filtered PRS readings as unchanged raw PRS readings when the raw PRS readings reach or vary outside of the predetermined range. A motion compensation function generated based on at least the filtered PRS readings can be used to correct a subject position and orientation (P&O) to compensate for the motion of the moving region of interest over time.

20 Claims, 7 Drawing Sheets

(51) Int. Cl.
*A61B 5/06* (2006.01)
*A61B 5/11* (2006.01)
*A61B 6/00* (2006.01)
*A61B 6/04* (2006.01)
*A61B 6/12* (2006.01)
*A61B 34/20* (2016.01)
*A61B 5/044* (2006.01)

(52) U.S. Cl.
CPC .......... *A61B 5/1114* (2013.01); *A61B 5/721* (2013.01); *A61B 6/04* (2013.01); *A61B 6/12* (2013.01); *A61B 5/02* (2013.01); *A61B 5/044* (2013.01); *A61B 5/066* (2013.01); *A61B 5/1107* (2013.01); *A61B 5/743* (2013.01); *A61B 34/20* (2016.02)

(58) Field of Classification Search
CPC ......... A61B 6/5264; A61B 5/062; A61B 5/06; A61B 5/044; A61B 5/743; A61B 5/066; A61B 34/20; A61B 5/1107; A61B 5/02
See application file for complete search history.

(56) References Cited

U.S. PATENT DOCUMENTS

| | | | |
|---|---|---|---|
| 7,343,195 B2 | 3/2008 | Strommer et al. | |
| 7,386,339 B2 | 6/2008 | Strommer et al. | |
| 7,811,294 B2 * | 10/2010 | Strommer | A61B 1/00147 606/108 |
| 7,840,252 B2 * | 11/2010 | Strommer | A61B 5/06 600/407 |
| 8,670,816 B2 * | 3/2014 | Green | A61B 8/0841 600/407 |
| 9,572,519 B2 * | 2/2017 | Shmarak | G06F 19/00 |
| 2005/0107688 A1 * | 5/2005 | Strommer | A61B 5/0066 600/424 |
| 2005/0251028 A1 | 11/2005 | Boese et al. | |
| 2006/0058647 A1 | 3/2006 | Strommer et al. | |
| 2007/0049817 A1 | 3/2007 | Preiss et al. | |
| 2007/0106457 A1 * | 5/2007 | Rosenberg | G01C 17/00 701/532 |
| 2008/0287805 A1 * | 11/2008 | Li | A61B 8/0833 600/471 |
| 2009/0043164 A1 * | 2/2009 | Hasegawa | A61B 1/00016 600/118 |
| 2009/0163800 A1 | 6/2009 | Xu | |
| 2009/0253985 A1 * | 10/2009 | Shachar | A61B 1/018 600/424 |
| 2010/0041949 A1 * | 2/2010 | Tolkowsky | A61B 1/0052 600/109 |
| 2010/0188371 A1 * | 7/2010 | Lowles | G06F 3/04886 345/178 |
| 2011/0158488 A1 * | 6/2011 | Cohen | A61B 6/12 382/128 |
| 2012/0165658 A1 * | 6/2012 | Shi | A61B 5/06 600/424 |
| 2012/0172702 A1 * | 7/2012 | Koyrakh | A61B 5/053 600/408 |

FOREIGN PATENT DOCUMENTS

| | | | |
|---|---|---|---|
| WO | WO 2004/103182 A1 | 2/2004 | |
| WO | WO 2007113719 A1 * | 10/2007 | ............ A61B 5/06 |
| WO | WO 2009/013661 A2 | 1/2009 | |
| WO | WO 2011/081688 A1 | 7/2011 | |
| WO | WO 2012109760 A1 * | 8/2012 | ............ G01B 7/003 |

OTHER PUBLICATIONS

International Preliminary Report on Patentability for PCT/US2010/050224 dated Jul. 4, 2012.

* cited by examiner

ENHANCED COMPENSATION OF MOTION IN A MOVING ORGAN USING PROCESSED REFERENCE SENSOR DATA

CROSS REFERENCE TO RELATED APPLICATIONS

This application claims the benefit of U.S. provisional application No. 61/807,511, filed 2 Apr. 2013 (the '511 application). This application is also related to U.S. application Ser. No. 12/650,932, filed 31 Dec. 2009 (the '932 application), now pending. The '511 application and the '932 application are both hereby incorporated by reference as though fully set forth herein.

BACKGROUND a. Field

The instant disclosure relates generally to medical devices and more particularly to systems and methods for medical imaging and navigation.

b. Background Art

Systems and methods for obtaining and displaying two-dimensional and three-dimensional images are known in the art, for example, as seen by reference to U.S. Pat. No. 7,386,339 entitled "MEDICAL IMAGING AND NAVIGATION SYSTEM" to Strommer et al., hereby incorporated by reference in its entirety. Strommer et al. disclose a medical imaging and navigation system that has a capability for constructing and displaying three-dimensional images of moving organs, synchronously with the actual movement of these organs and synchronously with an invasive surgical tool, such as a catheter. The system includes a medical positioning system (MPS) for ascertaining the location and orientation of multiple MPS sensors, a two-dimensional imaging system having an image detector for obtaining two-dimensional images of the moving organ and a superimposing processor. The MPS system includes a sensor mounted on the surgical tool and a sensor attached to the body of the patient for a positional reference ("Patient Reference Sensor", or PRS). The system acquires a plurality of two-dimensional images (and respective location/orientation data and organ timing data, e.g., ECG signal) and records the sets of positions and orientation of all sensors. The system reconstructs a three-dimensional image from the combination of 2-D images and sensor data. When a physician inserts the surgical tool into the body of the patient, the system also detects the location and orientation of the MPS sensor that is mounted on the tool. The superimposing processor super-imposes a representation of the surgical tool on the currently displayed two-dimensional and three-dimensional images, which may be played back in accordance with real-time ECG data.

The PRS is provided so that the sensors associated with the surgical tools remain in a co-registered coordinate system to the X-ray imager at all times. The system detects movements of the patient using the PRS (e.g., patient body movements and respiration induced movements). The movements (as sensed by the PRS) are used to shift the coordinate system relative to the coordinate system in which the two-dimensional images were acquired. Therefore, in Strommer et al., the projection of real-time location information on previously recorded 2-D or 3-D images is both ECG synchronized and respiration compensated. However, in some situations, there is little or no correlation between the external motion compensation signals being used (i.e., the ECG signal and the PRS readings) and the internal motion of a region of interest. For example only, in the case of atrial fibrillation, the ECG signal may not effectively serve as a predictor or correlation input for the motion of the atria.

There is therefore a need for a system and method for compensation for the motion of a moving organ that minimizes or eliminates one or more of the problems set forth above.

The foregoing discussion is intended only to illustrate the present field and should not be taken as a disavowal of claim scope.

SUMMARY

Motion compensation accuracy can be improved by detecting and selectively suppressing relatively small movements of a reference position sensor (e.g., patient reference sensor mentioned above), due to, for example only, skin movements or patient head movements. Embodiments consistent with the teachings of the present disclosure have the advantage of improved motion compensation accuracy.

In an embodiment, a method is provided for displaying a moving region of interest located within a body. The method includes obtaining an image of the moving region of interest at a first time. The method further includes acquiring a plurality of raw patient reference sensor (PRS) readings over time where the raw PRS readings indicate at least one of a position and an orientation of a PRS. The PRS is associated with the moving region of interest. The method further includes filtering the raw PRS readings and outputting filtered PRS readings. The filtering includes (i) outputting the filtered PRS readings as a baseline value while the raw PRS readings are within a predetermined range of the baseline value; and (ii) outputting the filtered PRS readings as unchanged raw PRS readings when the raw PRS readings reach or vary outside of the predetermined range of the baseline value. The method still further includes generating, using a computer processing apparatus, a motion compensation function based on at least the filtered PRS readings. The method still further includes determining, using a positioning system, a subject position and orientation of a medical device at a second time. The method still further includes correcting, using the computer processing apparatus, the subject position and orientation of the medical device using the motion compensation function to thereby compensate for the motion of the region of interest between the first time at which the image of the region of interest was acquired and the second time at which the subject position and orientation of the device was determined. The method also includes superimposing, using a superimposing processor, a representation of the medical device on the image in accordance with the corrected position and orientation.

In an embodiment, a method is provided for compensating for the motion of a moving region of interest located within a body. The method includes acquiring a plurality of raw patient reference sensor (PRS) readings over time where the raw PRS readings indicate at least one of a position and an orientation of a PRS. The PRS is associated with the moving region of interest. The method further includes processing the raw PRS readings, using a computer processing apparatus, to output filtered PRS readings. The processing includes: (i) outputting the filtered PRS readings as a baseline value while the raw PRS readings are within a predetermined range of the baseline value; and (ii) outputting the filtered PRS readings as unchanged raw PRS readings when the raw PRS readings reach or vary outside of the predetermined range of the baseline value. The method still further includes generating, using the computer processing apparatus, a motion compensation function based on at least the filtered PRS readings. The method further includes applying the motion compensation function to a subject position and orientation (P&O) associated with the moving region of interest to obtain a motion corrected P&O, to thereby correct for the motion of the moving region of interest between a first time associated with the subject P&O and a second time associated with the corrected P&O.

In an embodiment, an apparatus is provided for compensating for the motion of a moving region of interest located within a body. The apparatus includes a medical positioning system, and a patient reference sensor (PRS) coupled to the medical positioning system and configured to be associated with the moving region of interest. The positioning system is configured to acquire a series of raw PRS readings indicative of at least one of a position and an orientation of the PRS over time. The apparatus further includes means for filtering the raw PRS readings and outputting filtered PRS readings. The filtering means if configured to (i) output filtered PRS readings as a baseline value while the raw PRS readings are within a predetermined range of the baseline value; and (ii) output filtered PRS readings as unchanged raw PRS readings when the raw PRS readings reach or vary outside of the predetermined range of the baseline value. The apparatus further includes means for generating a motion compensation function based on at least the filtered PRS readings, and means for correcting a subject position and orientation (P&O) using the motion compensation function to thereby compensate for the motion of the moving region of interest between a current time for which the subject P&O is being corrected and an earlier time.

The foregoing and other aspects, features, details, utilities, and advantages of the present disclosure will be apparent from reading the following description and claims, and from reviewing the accompanying drawings.

DETAILED DESCRIPTION

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment," or the like, means that a particular feature, structure, or characteristic described in connection with the embodiment is included in at least one embodiment. Thus, appearances of the phrases "in various embodiments," "in some embodiments," "in one embodiment," or "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of a medical device or instrument used to treat a patient. The term "proximal" refers to the portion of the device closest to the clinician (or to a robotic control configured to manipulate the device) and the term "distal" refers to the portion located furthest from the clinician. It will be further appreciated that for conciseness and clarity, spatial terms such as "vertical," "horizontal," "up," and "down" may be used herein with respect to the illustrated embodiments. However, medical devices may be used in many orientations and positions, and these terms are not intended to be limiting or absolute.

Figure 1:
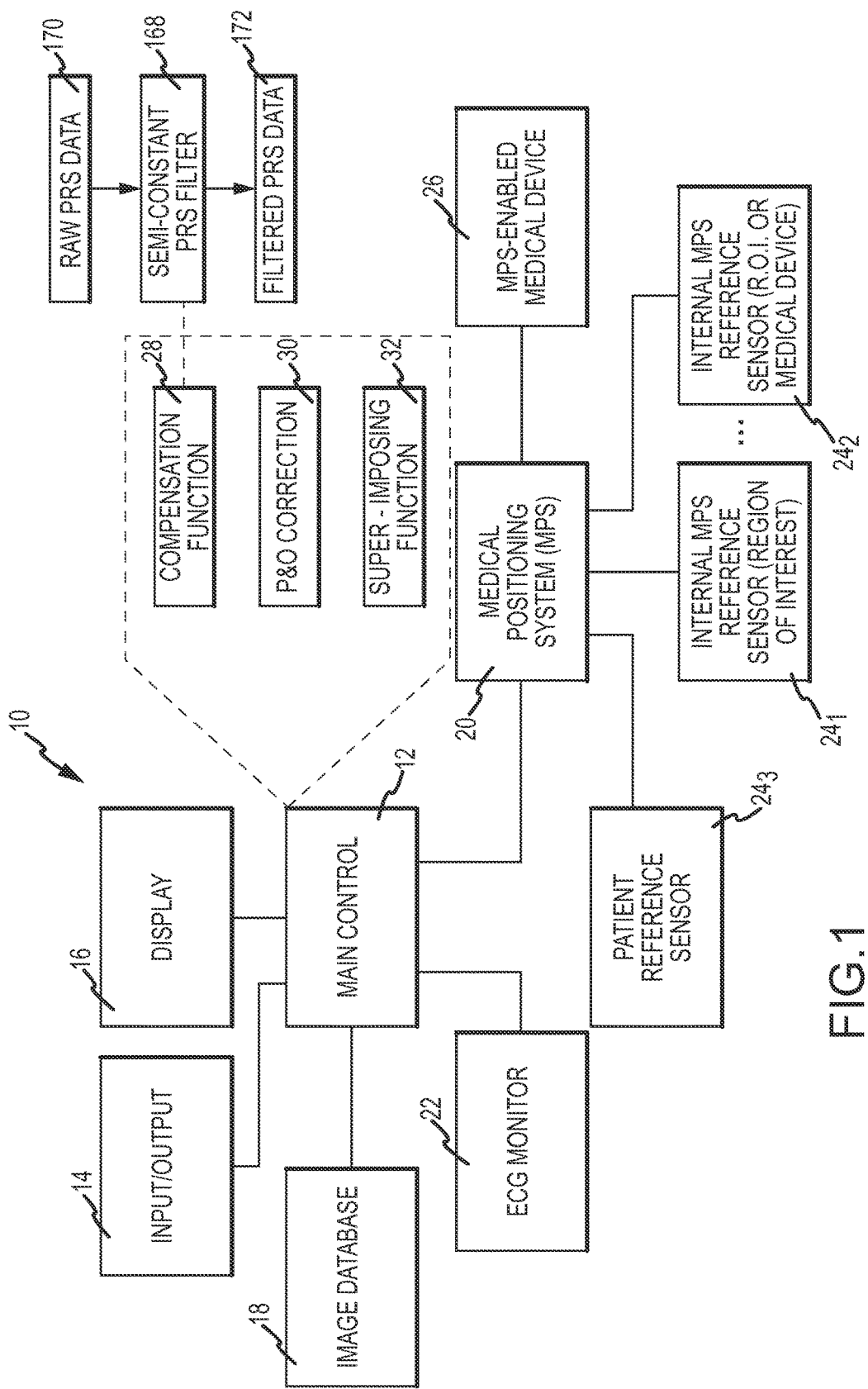
FIG. 1 is a schematic and block diagram view of a system incorporating an embodiment for compensation of motion in a moving organ.

Referring now to the drawings wherein like reference numerals are used to identify identical components in the various views, FIG. 1 is a diagrammatic view of a system 10 in which aspects of the disclosure may be embodied. It should be understood that while embodiments of the disclosure will be described in connection with a magnetic field-based positioning system deployed in connection with a fluoroscopy-based imaging system, such an embodiment is exemplary only and not limiting in nature.

Before proceeding to a detailed description keyed to the drawings, a general overview concerning motion compensation will be set forth. As a starting point, there is a desire to reduce a patient's exposure to x-rays, such as may be used in fluoroscopy. It is therefore desirable to be able to use, and reuse to the greatest extent possible, an image (or a sequence of images defining a cine loop) of a region of interest acquired in the past. This will reduce the need for continuous exposure or subsequent additional exposures for the purpose of acquiring updated imaging. Navigation of a medical instrument using the previously-acquired image or cine-loop is made possible by ascertaining the position and orientation (P&O) of the instrument and then superimposing a projection of that instrument's P&O onto the image. A problem arises over time, however, because both the patient as well as his or her internal organs can move (e.g., beating heart), changing positions relative to the time at which the image was taken. Absent compensation for these varying types of motion, the P&O readings reflecting the real time position of the medical instrument would be inaccurately represented on the image (i.e., the representation could be superimposed in the "wrong" location on the image). U.S. Pat. No. 7,386,339 referred to in the Background discloses motion compensation for patient movements and respiration-induced movements by providing a patient reference sensor (PRS). By interpreting P&O readings that track the motion of a catheter relative to the P&O readings of the PRS, a certain type of motion compensation can be achieved. In other words, the movements detected by the PRS shift the coordinate system relative to the coordinate system in which the two dimensional images were acquired. However, as also described in the Background, the PRS P&O readings may have little or no correlation to the movements of an internal moving organ.

With continued reference to FIG. 1, the system 10 as depicted includes a main electronic control 12 having various input/output mechanisms 14, a main display 16, an image database 18, a localization system such as a medical positioning system (MPS) system 20, an ECG monitor 22, a plurality of MPS position reference sensors designated $24_1$, $24_2$ and $24_3$, and an MPS-enabled medical device 26 (which itself includes a position reference sensor). The MPS-enabled device 26 may be any interventional device or delivery tool. For example, the device 26 may include guidewires, stylets, cannulation catheters, EP catheters and the like.

The main electronic control 12, in a computer-implemented embodiment, includes a computer processing apparatus that can be configured via programming to perform a plurality of functions, including those shown in block form in FIG. 1: a motion compensation function 28 (and associated filtering function blocks 168, 170, 172 as described below), a position and orientation (P&O) correction function 30 and an image super-imposing function 32. The main electronic control 12 is configured generally to generate data to be displayed (e.g., single image or sequence of images) corresponding to a moving region of interest (ROI) located within the body of a patient. The main electronic control 12 is specifically configured (by way of function blocks 28, 30 and 32) to accurately superimpose a representation of a tracked, MPS-enabled medical device 26 on a previously acquired image (or sequence) for display on the display 16, compensated for the motion of a moving region of interest. The input/output mechanisms 14 may comprise conventional apparatus for interfacing with a computer-based control, for example, a keyboard, a mouse, a tablet or the like. The display 16 may also comprise conventional apparatus.

With continued reference to FIG. 1, the system 10, in an embodiment, includes a semi-constant PRS (SCP) filter block 168 configured to process raw PRS readings, indicated by block 170, and output filtered PRS readings, indicated by block 172. The SCP filter block 168 reduces or eliminates the adverse effects of small movements of a reference sensor, such as the patient reference sensor (PRS), due to small skin movements and/or patient head movements. Embodiments of an SCP filter will be set forth below in greater detail in connection with FIGS. 5-7.

The image database 18 is configured to store image information of relating to the patient's body, including the moving region of interest, and which may comprise (1) one or more two-dimensional still images acquired at respective, individual times in the past; (2) a plurality of related two-dimensional images obtained in real-time from an image acquisition device (e.g., fluoroscopic images from an x-ray imaging apparatus, such as that shown in exemplary fashion in FIG. 2) wherein the image database acts as a buffer (live fluoroscopy); and/or (3) a sequence of related two-dimensional images defining a cine-loop (CL) wherein each image in the sequence has at least an ECG timing parameter associated therewith adequate to allow playback of the sequence in accordance with acquired real-time ECG signals obtained from the ECG monitor 22. It should be understood that the two-dimensional images may be acquired through any imaging modality, now known or hereafter developed, for example X-ray, ultra-sound, computerized tomography, nuclear magnetic resonance or the like.

The MPS system 20 is configured to acquire positioning (localization) data (i.e., position and orientation—P&O) of one or more MPS sensors. The P&O may be expressed as a position (i.e., a coordinate in three axes X, Y and Z) and orientation (i.e., an azimuth and elevation) of the magnetic field sensor in the magnetic field relative to a magnetic field generator(s)/transmitter(s).

The internal MPS position reference sensor $24_1$ is associated with a moving region of interest (ROI) in the body, which may be a moving organ, and more specifically may be the heart and/or chambers or portions thereof (e.g., atria). The internal position reference sensor $24_1$ is associated with the ROI in such a way that it will move together with the moving ROI, and thus fairly indicate the motion of the region of interest. Generally, associating the sensor $24_1$ with the region of interest (ROI) may be done in any one or more ways: (1) placing the sensor $24_1$, or an interventional device like a catheter carrying the sensor $24_1$, in an anatomical area where it is held by the anatomy itself, for example, a catheter that has been maneuvered in a tubular organ like the coronary sinus; (2) fixing the sensor $24_1$, or an interventional device like a catheter carrying the sensor, to the anatomy in the region of interest using a fixation mechanism, active or passive, for the duration of the procedure; (3) holding the sensor $24_1$, or an interventional device like a catheter carrying the sensor, in steady contact with the anatomy in the region of interest; and (4) placing sensor $24_1$ (or interventional device carrying the sensor) in a non-MPS-enabled device that is in turn affixed to the anatomy in the region of interest. As to approach (2), where the region of interest is the heart, an example may include placing the sensor $24_1$ epicardially in the surface of the heart. As to approach (3), an example may include associating the sensor $24_1$ with a catheter that is maneuvered into steady contact with the heart interior. As to approach (4), an example may include placing an MPS-enabled guidewire (having the sensor $24_1$) in the lumen of a pacing lead that is in turn affixed to the tissue of a heart chamber.

One or more additional, optional internal position sensors may be provided, for example, as shown by sensor $24_2$. The additional one or more sensors $24_2$ may be associated with either or both of the (1) the moving region of interest; or (2) the medical device 26. The additional sensors $24_2$, are configured to provide additional data points (P&O readings) with respect to either the moving region of interest or medical device, as the case may be, thereby providing addition information concerning their respective motions over time.

The patient reference sensor (PRS) $24_3$ is configured to provide a stable, positional reference of the patient's body so as to allow motion compensation for gross patient body movements and/or respiration-induced movements, as described above. The PRS $24_3$ may be attached to the patient's manubrium sternum, a stable place on the chest, or other location that is relatively positionally stable.

In a magnetic field-based embodiment, the P&O may be based on capturing and processing the signals received from the magnetic field sensor while in the presence of a controlled low-strength AC magnetic field. Accordingly, the internal sensors may each comprise one or more magnetic field detection coil(s), and it should be understood that variations as to the number of coils, their geometries, spatial relationships, the existence or absence of cores and the like are possible. From an electromagnetic perspective—all sensors are created equal: voltage is induced on a coil residing in a changing magnetic field, as contemplated here. The sensors 24 are thus configured to detect one or more characteristics of the magnetic field(s) in which they are disposed and generate an indicative signal, which is further processed to obtain the P&O thereof. For one example of a sensor, see U.S. Pat. No. 7,197,354 entitled SYSTEM FOR DETERMINING THE POSITION AND ORIENTATION OF A CATHETER issued to Sobe, hereby incorporated by reference in its entirety.

The electro-cardiogram (ECG) monitor 22 is configured to continuously detect an electrical timing signal of the heart organ through the use of a plurality of ECG electrodes (not shown), which may be externally-affixed to the outside of a patient's body. The timing signal generally corresponds to the particular phase of the cardiac cycle, among other things. The ECG signal may be used by the main electronic control 12 for ECG synchronized play-back of a previously captured sequences of images (cine loop). The ECG monitor 22 and ECG-electrodes may comprise conventional components.

Figure 2:
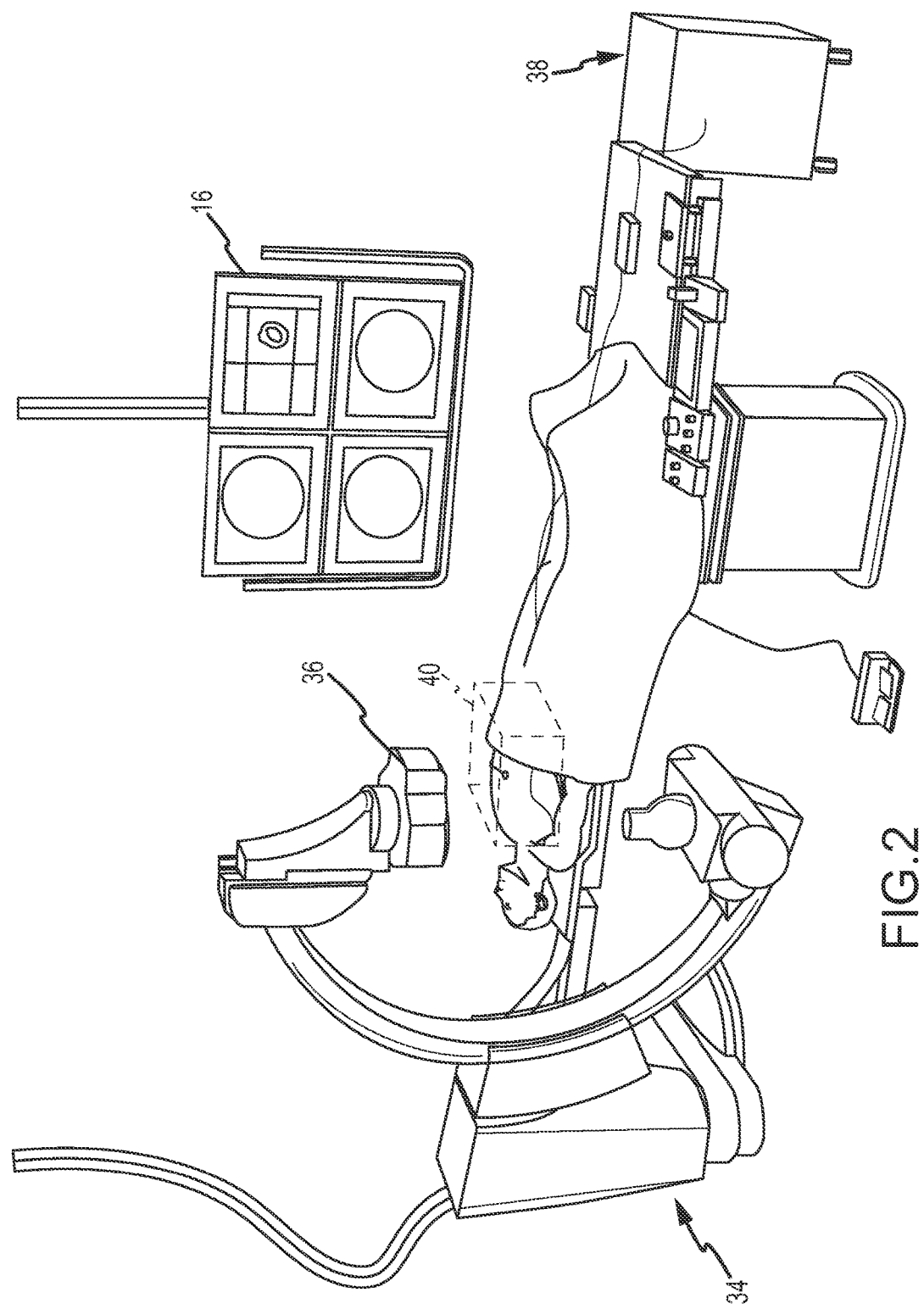
FIG. 2 is a diagrammatic view of the system of FIG. 1, in a fluoroscopy-based imaging embodiment.

FIG. 2 is a diagrammatic view of an embodiment which includes a self-contained imaging capability, along with motion compensation. More specifically, the system 10 is shown as being incorporated into an fluoroscopic imaging system 34, which may include commercially available fluoroscopic imaging components (i.e., "Catheter Lab"). The MPS system 20, in a magnetic field-based embodiment, includes a magnetic transmitter assembly (MTA) 36 and a magnetic processing core 38 for determining position and orientation (P&O) readings. The MTA 36 is configured to generate the magnetic field(s) in and around the patient's chest cavity, in a predefined three-dimensional space designated a motion box 40 in FIG. 2. The MPS sensors $24_i$ (where i=1, 2, . . . , n) as described above are configured to sense one or more characteristics of the magnetic field(s) and when the sensors are in the motion box 40, each generate a respective signal that is provided to the magnetic processing core 38. The processing core 38 is responsive to these detected signals and is configured to calculate respective three-dimensional position and orientation (P&O) readings for each MPS sensor $24_i$ in the motion box 40. Thus, the MPS system 20 enables real-time tracking of each sensor $24_i$ in three-dimensional space. In the illustrated embodiment, the positional relationship between the image coordinate system and the MPS coordinate system may be calculated based on a known optical-magnetic calibration of the system (e.g., established during setup), since the positioning system and imaging system may be considered fixed relative to each other in such an embodiment. However, for other embodiments using other imaging modalities, including embodiments where the image data is imported from an external source, a registration step may need to be performed initially. One exemplary embodiment of an MPS system 20 will be described in greater detail below in connection with FIG. 4.

The main electronic control 12, as configured by way of super-imposing function block 32, includes the capability of producing (and superimposing) a projection of the real-time location information (P&O) of a medical device on previously recorded x-ray images or in the case of cine-loops (CL), onto each image in the sequence. In addition, with the availability of the ECG signal and a PRS position signal, the main electronic control 12 can replay a cine loop in an ECG synchronized and respiration-induced motion compensated manner. In a specific case of ECG synchronizing playback of a cine loop of the heart, the sequence is replayed in concordance with a real-time ECG signal (cardiac phase) of the patient. The main electronic control 12 may also be configured to include a respiration compensation algorithm configured to learn the motion induced by the patient's respiration, based on P&O readings from the PRS. The main electronic control 12 then calculates a respiration correction factor to apply to P&O measurements that are to be projected onto a sequence of cine-loop images. The PRS position signal allows for motion compensation for any patient's body movements, as the medical device's position (i.e., P&O measurement) may preferably be taken relative to the P&O measurements from the PRS.

However, as noted above, there are situations where there is very little or no correlation between the internal motion of the region of interest and the external signals (i.e., ECG signals and PRS signal) conventionally used for motion compensation. For example, in the case of atrial fibrillation, the ECG signal cannot serve as a predictor or correlation input for the motion of the atria.

Accordingly, one or more of the internal (i.e., inside the body) position reference sensors (e.g., sensor $24_1$) are located in the vicinity of the region of interest, or are otherwise associated with the region of interest (e.g., affixed) such that the internal MPS reference sensor moves together with the region of interest over time. As the region of interest moves, the MPS system 20 acquire a series of location (i.e., position and orientation) readings from the sensor. The motion compensation function block 28 (FIG. 1) determines the motion of the sensor (e.g., sensor $24_1$) according to acquired series of P&O readings. The block 28 further determines the motion of the region of interest based on the motion of the sensor, which may have a direct correspondence.

Figure 3B:
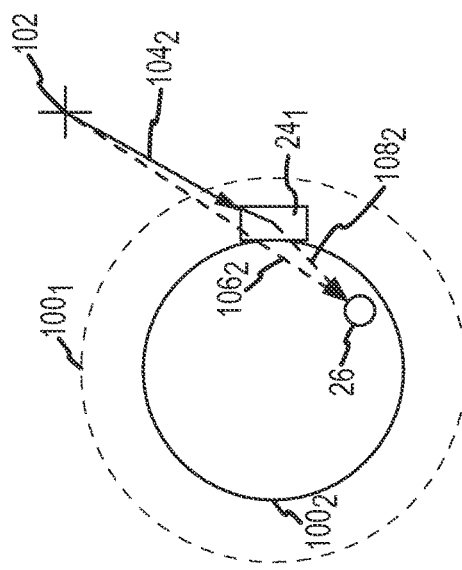
FIGS. 3A-3C are plan views showing the motion of a moving organ and the corresponding motion of an internal position reference sensor.
Figure 3C:
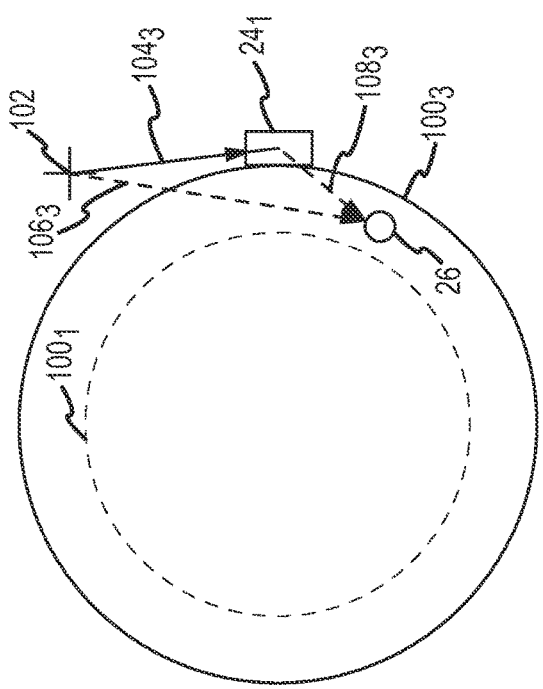
Figure 3A:
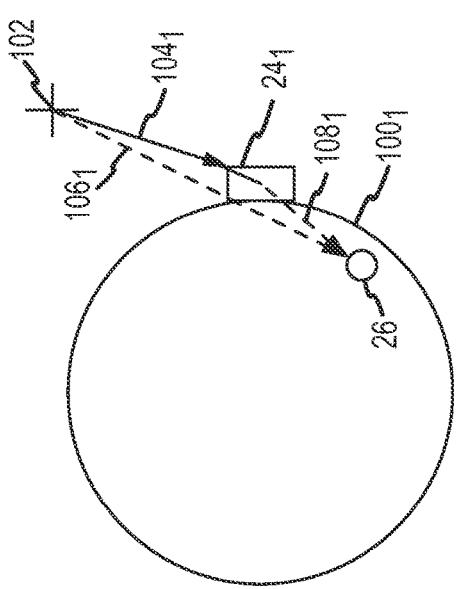

FIGS. 3A-3C are schematic diagram views of a region of interest, generally referenced 100, at three different activity states (states of movement), designated $100_1$, $100_2$ and $100_3$. In FIGS. 3A-3C, an internal MPS position reference sensor $24_1$ is placed in the vicinity of the region of interest 100 (e.g., at the orifice of the superior vena cava). In FIGS. 3A-3C, the region of interest 100 is depicted as a circle for simplicity.

In FIG. 3A, the region of interest $100_1$ is at a first activity state. The MPS system 20 detects a first position of the sensor $24_1$ at the first activity state. This first position (P&O) is represented as a vector $104_1$ relative to an arbitrary origin 102. The arbitrary origin 102 may be, for example, the location of the MTA 36 in the MPS system 102, a location on the motion box 40 or any other known location.

In FIG. 3B, the region of interest $100_2$ is at a second activity state, which as shown is contracted relative to the first activity state. The MPS system 20 detects a second position (i.e., position and orientation) $104_2$ of the sensor $24_1$. Note that the sensor $24_1$ moves with the region of interest as it moves.

In FIG. 3C, the region of interest $100_3$ is at a third activity state, which as shown is expanded relative to the first activity state. The MPS system 20 detects a third position (P&O) $104_3$ of the sensor $24_1$.

The series of detected first, second and third positions $104_1$, $104_2$ and $104_3$ of the sensor $24_1$ acquired by the MPS system 20 over time defines not only the motion of the sensor itself but also defines the motion of the region of interest. The motion compensation function block 28 may determine the motion of the region of interest 100 directly in accordance with the motion of the sensor $24_1$. This same motion can be assumed to influence the motion of the medical device 26, provided predefined criteria are met.

The criteria include verifying that an adequate level of correlation exists between the motion of the medical device 26 and the motion of the region of interest 100. One approach to verifying correlation is to compare the respective motions relative to a common time-line. For example, over some time interval, the system 10 may track the motion of the device 26, as indicated by the detected P&O's $106_1$, $106_2$ and $106_3$ shown in FIGS. 3A-3C, in addition to tracking the motion of the internal position sensor $24_1$. The system 10 compares the two motions and when the level of correlation exceeds a predetermined threshold, the correlation level is deemed adequate (predetermined criteria satisfied). In this regard, overall, the kind of correlation that is deemed adequate will vary; however, the ultimate goal is to reduce the amount of error (e.g., as expressed in millimeters). For this purpose (with the end goal in mind), correlation approaches may be determined empirically (e.g., bench testing). It should be further understood that the effect of the correlation threshold on the received error will also depend on the types of motions involved. Accordingly, motion compensation/correction will be performed.

The system 10 may additionally verify that a minimum level of correlation exists between the motion of the device 26 and the other compensation signals described above (i.e., the ECG signal(s) as well as the PRS signal). If there is only poor correlation between the motion of the device 26 and these compensation signals then compensation will not be performed at all. When motion correlation has been verified, the assumption that the motion of the region of interest will influence the motion of the device 26 can be relied on. After correlation has been verified, the MPS system 20 is then enabled to provide motion compensation.

Generate Motion Compensation Function. The MPS system 20 will generate data adequate to track the motion of a moving region of interest over time (e.g., via the internal sensor $24_1$) and allow the compensation function block 28 to generate a time varying motion compensation function. Just as the detected movements of the PRS allows shifting of the coordinate system (as described in U.S. Pat. No. 7,386,339), the motion of the internal sensor (e.g., sensor $24_1$) provides data adequate to implement a similar compensation function. For example in FIGS. 3A-3C, the position of the medical device 26 moves as the region of interest contracts (FIG. 3B) and expands (FIG. 3C). The relative displacement of the medical device 26 relative to the sensor $24_1$ (and thus also to the region of interest 100) is shown as vectors $108_1$, $108_2$ and $108_3$. Thus, one indication of the medical device's position is that taken relative to the sensor $24_1$.

The compensation function produced based on the motion of the sensor $24_1$ is a time-varying spatial function which accounts for the motion of the region of interest between a first time (at which the image was acquired) and a second time (at which the P&O of the device was measured). Assume that a two-dimensional image was acquired at a time when the region interest was in the first activity state $100_1$ (i.e., FIG. 3A). In this instance, a measured P&O of the device 26 would not need any motion compensation, at least not any to compensate for the motion of the region of interest. However, when the region of interest moves to the second activity state $100_2$, motion compensation is required to accurately project the measured P&O onto an image acquired at a time when the region of interest was at the first activity state (in this example). The compensation function evaluated at the time of the second activity state is a displacement vector that compensates for the motion of the region of interest between the given time (i.e., time of the measured device P&O—the time of the second activity state) and the time of the image (i.e., the time the image was acquired—the time of the first activity state). Likewise, the compensation function evaluated at the time of the third activity state $100_3$ is a displacement vector to compensate for motion between the given time (i.e., the time of the measured device P&O—the time of the third activity state) and the time of the image (i.e., the time the image was acquired—the time of the first activity state).

In sum, for a given spatial position (measured P&O) of the device 26 for a given time, the compensation function will constitute a vector displacement (and potentially rotation) by which the measured P&O of the MPS-enabled device 26 has to be corrected to match a given time in the past (i.e., at which the image was acquired). The displacement vector may be weighted in accordance with a weighting factor, which in turn may be calculated based on the calculated correlation level described above. Motion compensation approaches may be used as disclosed in U.S. Pat. No. 7,386,339 referred to above as well U.S. Pat. No. 7,343,195 (application Ser. No. 09/949,160 filed Sep. 7, 2001) entitled "METHOD AND APPARATUS FOR REAL TIME QUANTITATIVE THREE-DIMENSIONAL IMAGE RECONSTRUCTION OF A MOVING ORGAN AND INTRA-BODY NAVIGATION" to Strommer et al., the entire disclosures of both U.S. patents being hereby incorporated by reference herein.

P&O Correction. The P&O correction block 30 is configured to correct the P&O reading obtained at the given time using the compensation function. P&O correction function 30 adjusts the measured P&O of the medical device in accordance with the calculated displacement vector (and potentially rotation) described above.

Projection. Finally, a projection of the corrected P&O (three-dimensional) is made onto the two-dimensional image, with a representation of the medical device being superimposed on the image (e.g., may be cross-hairs representing the tip of a catheter or other representation). The resulting image may then be displayed on the display 16. One approach for projecting the corrected P&O onto a 2-D image is a direct consequence of the association of the MPS 3D coordinate system with the X-ray 2D coordinate system, as seen by reference to U.S. Pat. Pub. 2006/0058647, application Ser. No. 11/233,420 entitled METHOD AND SYSTEM FOR DELIVERING A MEDICAL DEVICE TO A SELECTED POSITION WITHIN A LUMEN, to Strommer et al., hereby incorporated by reference in its entirety. Once the coordinate systems are co-registered (a process that may be referred to a magnetic-optical calibration, which may be performed at the installation of the MPS system 20, as noted above), the coordinates of any 3D object (e.g., sensor, landmark or other artifacts) which needs to be displayed on a 2D image are multiplied by a coordinate transformation matrix that computes the corresponding 2D coordinates on the displayed image. This approach is exemplary only and not limiting in nature.

Multiple Inputs, Internal Sensors. In embodiments where the external PRS and/or additional internal position reference sensor inputs are used for motion compensation, the compensation function block 28 implements a composite motion compensation function that is formed by the summation of individual motion compensation contributions, i.e., the individual displacement vectors and (potentially rotations) attributable to each motion/sensor input (provided that correlation requirements are met, as described above). For example, additional sensors may be located on the medical device 26 or other medical devices and/or tools, for example, another MPS sensor disposed on a catheter, guidewire, etc. The P&O readings from additional internal sensors may reveal other movements or other aspects to the movements of the region of interest and/or the medical device.

The composite compensation function, for example, may include a number of terms where each term corresponds to an input, i.e., one term being provided with respect to the PRS, another term being provided with respect to the internal sensor $24_1$, still another term being provided with respect to an additional sensor $24_2$, and so on. In another embodiment, the inputs from the PRS, the ECG signals and the one or more internal MPS reference sensors may be used in combination to provide for robust motion compensation. In these embodiments, the individual inputs are weighted by a respective weighting factor to form a composite motion compensation function. The respective level of correlation is a principal factor according to which each weighting factor is determined. The weighted function can be depicted as weighted vector summation of the compensation function vectors.

Figure 4:
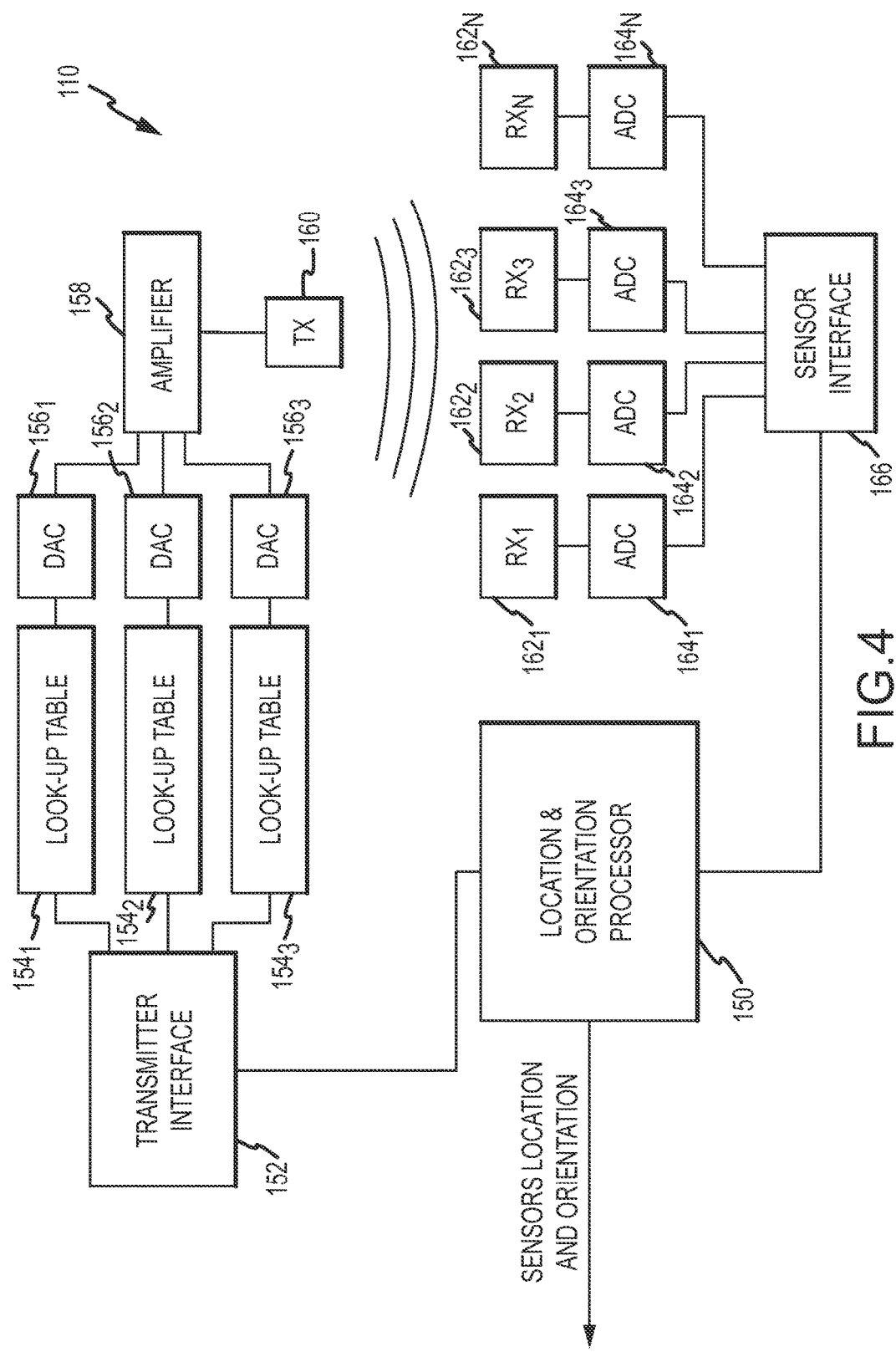
FIG. 4 is a schematic and block diagram view of one exemplary embodiment of a medical positioning system (MPS) as shown in block form in FIG. 1.

FIG. 4 is a schematic and block diagram of one exemplary embodiment of MPS system 20, designated as an MPS system 108, as also seen by reference to U.S. Pat. No. 7,386,339, referred to above, and portions of which are reproduced below. It should be understood that variations are possible, for example, as also seen by reference to U.S. Pat. No. 6,233,476 entitled MEDICAL POSITIONING SYSTEM, also hereby incorporated by reference in its entirety. This description is exemplary only and not limiting in nature.

MPS system 110 includes a location and orientation processor 150, a transmitter interface 152, a plurality of look-up table units $154_1$, $154_2$ and $154_3$, a plurality of digital to analog converters (DAC) $156_1$, $156_2$ and $156_3$, an amplifier 158, a transmitter 160, a plurality of MPS sensors $162_1$, $162_2$, $162_3$ and $162_N$, a plurality of analog to digital converters (ADC) $164_1$, $164_2$, $164_3$ and $164_N$ and a sensor interface 166.

Transmitter interface 152 is connected to location and orientation processor 150 and to look-up table units $154_1$, $154_2$ and $154_3$. DAC units $156_1$, $156_2$ and $156_3$ are connected to a respective one of look-up table units $154_1$, $154_2$ and $154_3$ and to amplifier 158. Amplifier 158 is further connected to transmitter 160. Transmitter 160 is also marked TX. MPS sensors $162_1$, $162_2$, $162_3$ and $162_N$ are further marked $RX_1$, $RX_2$, $RX_3$ and $RX_N$, respectively. Analog to digital converters (ADC) $164_1$, $164_2$, $164_3$ and $164_N$ are respectively connected to sensors $162_1$, $162_2$, $162_3$ and $162_N$ and to sensor interface 166. Sensor interface 166 is further connected to location and orientation processor 150.

Each of look-up table units $154_1$, $154_2$ and $154_3$ produces a cyclic sequence of numbers and provides it to the respective DAC unit $156_1$, $156_2$ and $156_3$, which in turn translates it to a respective analog signal. Each of the analog signals is respective of a different spatial axis. In the present example, look-up table $154_1$ and DAC unit $156_1$ produce a signal for the X axis, look-up table $154_2$ and DAC unit $156_2$ produce a signal for the Y axis and look-up table $154_3$ and DAC unit $156_3$ produce a signal for the Z axis.

DAC units $156_1$, $156_2$ and $156_3$ provide their respective analog signals to amplifier 158, which amplifies and provides the amplified signals to transmitter 160. Transmitter 160 provides a multiple axis electromagnetic field, which can be detected by MPS sensors $162_1$, $162_2$, $162_3$ and $162_N$. Each of MPS sensors $162_1$, $162_2$, $162_3$ and $162_N$ detects an electromagnetic field, produces a respective electrical analog signal and provides it to the respective ADC unit $164_1$, $164_2$, $164_3$ and $164_N$ connected thereto. Each of the ADC units $164_1$, $164_2$, $164_3$ and $164_N$ digitizes the analog signal fed thereto, converts it to a sequence of numbers and provides it to sensor interface 166, which in turn provides it to location and orientation processor 150. Location and orientation processor 150 analyzes the received sequences of numbers, thereby determining the location and orientation of each of the MPS sensors $162_1$, $162_2$, $162_3$ and $162_N$. Location and orientation processor 150 further determines distortion events and updates look-up tables $154_1$, $154_2$ and $154_3$, accordingly.

It should be understood that variations and other uses other than for the described imaging embodiments are possible. High-fidelity device positioning as provided through the motion compensation embodiments described herein may be used for alternate purposes such as for placing accurate landmarks (i.e., to serve as navigation references of other devices), for co-registration with other modalities (e.g., Ensite™ NavX™, computed tomography (CT)), as well as for determining when or distinguishing between a "real" motion (i.e., like the actual moving of a catheter by the physician) has occurred versus what seems to be motion but is actually an external event, such as patient motion.

Optional Semi-Constant Patient Reference Sensor Filter. In various embodiments, the raw data output from a reference sensor, such as the patient reference sensor (PRS), for example the PRS $24_3$ in FIG. 1, may be optionally filtered (e.g., replaced by filtered data), at or alternatively without the user's discretion. As noted above and with reference to FIGS. 3A-3C, the PRS $24_3$ is configured to provide a stable, positional reference of the patient's body so as to allow motion compensation for gross patient body movements and/or respiration-induced movements. The PRS $24_3$ may be attached to the patient's manubrium sternum, a stable place on the chest, or other location that is relatively positionally stable. In order to enhance system performance, it is desirable that the PRS not be moved notably during the procedure, except for those types of movements it is intended to detect (e.g., patient movements and respiration induced motion). However, for example only and not by way of limitation, a patient's head movement(s) and/or physician manipulation of surgical tools via a superior (chest) approach may cause such an undesired shift (movement) of the PRS, which in turn causes its output to also shift. Subsequent use of such shifted PRS output may cause undesired results in motion compensation processing.

In one embodiment, a comfortable pillow can be used to help reduce the head motion described above. This has the result of reducing the undesired shifting of the PRS mentioned above. In another embodiment, a filter configured to process the raw PRS output is provided to screen out relatively small unintentional movements of the PRS. The filter has the effect of suppressing such unintentional movements of the PRS in the PRS output. It should be appreciated additional embodiments may be provided, for example, that the above-mentioned filter can be used in addition to use of other PRS shift-reducing devices, such as the pillow described above, to screen unintentional skin movements in the vicinity of the PRS.

With regard to the above-mentioned filtering approach, in an embodiment, a so-called Semi-Constant PRS (SCP) filter may be provided, which is shown as semi-constant PRS filter block 168 in FIG. 1 (hereinafter referred to as the SCP filter 168). The SCP filter 168 is configured to receive raw (i.e., unfiltered) PRS readings 170 obtained from the MPS 20 that indicate the position and/or orientation of the PRS and then output filtered PRS readings 172. The SCP filter 168 may utilize an algorithm or computer program embodied or stored in a computer readable medium (e.g., memory), which may be executed by an electronic processor (e.g., the main electronic control 12 or a similar computer processing apparatus contained in the medical positioning system 20). Overall, the SCP filter 168 is configured to filter out small movements reflected in the raw PRS readings, which as noted above can be the result of unintentional skin movement near the PRS, patient head movement, or the like. The filtering action of the SCP filter 168 is intended to improve PRS position and orientation accuracy by compensating for patient skin movements on the order of (i.e., up to) approximately 1 centimeter (10 millimeters) or less in an embodiment. This improved accuracy is useful in many motion compensation applications, for example only, improving the cine loop projection/superimposing even while unintentional skin movements or head movements are impacting the PRS output(s).

The SCP filter 168 may be advantageously adapted for use in connection with chest accessed (superior) procedures. In such procedures, medical or surgical tool manipulations performed by the physician as part of the procedure, may result in additional skin movements in the vicinity of the PRS, which more rarely occur in the event of groin access. A typical example where the SCP filter 168 may be effective is a procedure practicing superior introduction of tools. In at least one embodiment, the SCP filter 168 may be selected by the user, if and when he/she finds it to be useful and/or effective. That is, if a user wishes to activate operation of the SCP filter 168, he/she can manually enable it via a relevant graphical user interface (GUI), such as a screen/mouse combination, pedal, or other facilities known in the art.

The SCP filter 168, in at least one embodiment, may employ a hysteresis filter concept. Accordingly, the concept of hysteresis (e.g., a system's dependence not only on its current environment but also on its past environment) may be used to filter signals so that the output reacts slowly by taking recent history into account.

Figure 5:
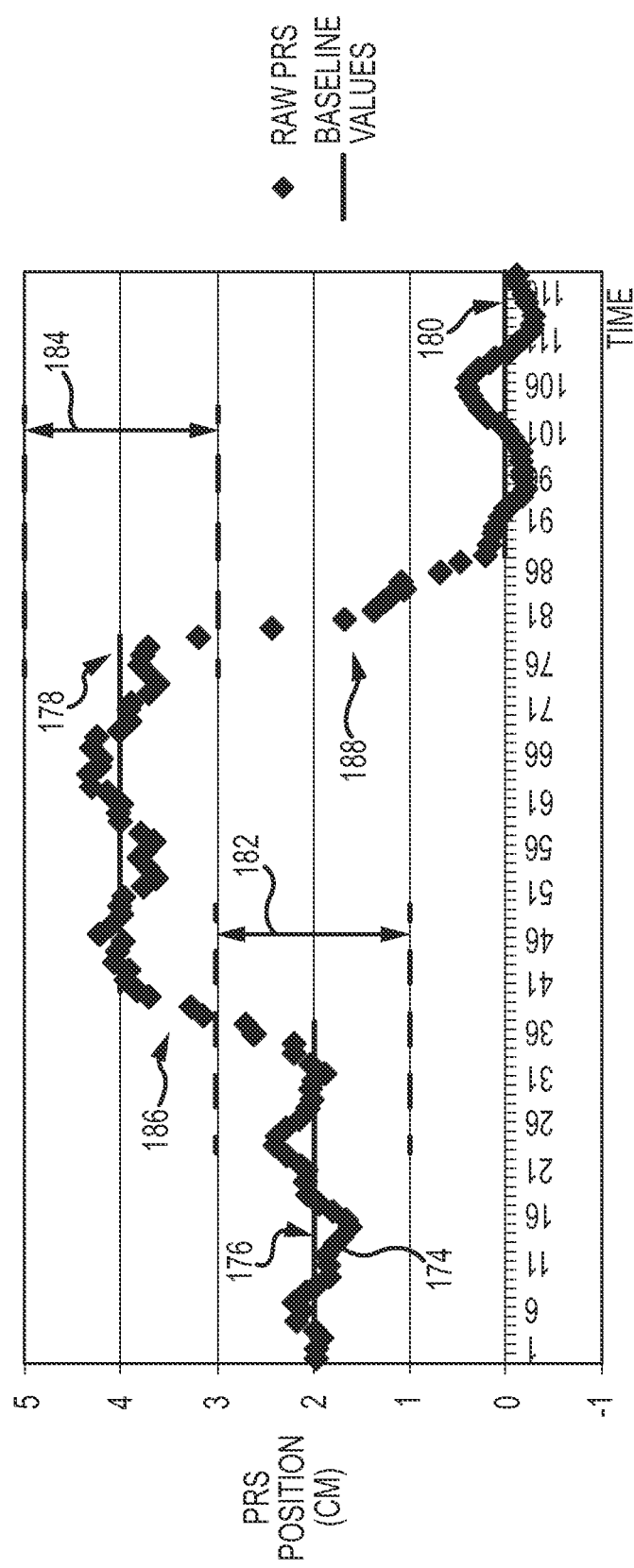
FIG. 5 is a graph of patient reference sensor (PRS) data versus time showing, in an embodiment, several baseline positions, threshold amounts surrounding the baseline positions, and transient periods.

FIG. 5 is a graph showing a plurality of raw PRS readings 174 versus time. In this regard, the raw PRS readings 174 are plotted on the Y-axis as a position, for example, as a distance in centimeters relative to a predefined datum plane. The X-axis is delineated in units of time. Without loss of generality, the raw PRS readings 174 are shown as being a position in a single dimension; however, it should be appreciated that such PRS readings 174 may comprise, in different embodiments, one or more of plural position and/or orientation parameters. For example only, a raw PRS reading may express a position (i.e., a coordinate in three axes X, Y and Z) and/or an orientation (i.e., roll, yaw and pitch) of the PRS relative to an origin of a reference coordinate system (e.g., a magnetic field generator(s) or transmitter(s), in an embodiment). For six degree of freedom (6DOF) processing, a raw PRS reading may comprise a three-dimensional coordinate (three axes X, Y, Z) along with all three orientation angles. Alternatively, where only a single axis (1DOF) is of interest, the raw PRS reading (or relevant portion thereof) may comprise just the single axis of interest. In sum, while FIG. 5 is presented as involving only a single axis (1DOF), this is for clarity of illustration only, and not by way of limitation.

With continued reference to FIG. 5, several items are specifically identified to help understand the PRS filter 168 and its function, when active. In this regard, plural baseline positions and/or orientations are shown as constant PRS value lines (i.e., horizontally-extending lines), which are respectively designated as a first baseline value 176, a second baseline value 178, and a third baseline value 180. Each baseline value 176, 178, 180 is surrounded by respective upper and lower thresholds. Each pair of upper/lower thresholds define respective predetermined ranges, two of which are shown (e.g., ranges 182, 184). In the illustrated embodiment, the upper and lower thresholds are evenly set above and below the constant baseline value, although it should be understood that this characteristic, while typical, is not required. The SCP filter 168 is semi-constant in the sense that at different times, the output filtered PRS readings may assume different, yet constant, values. The raw PRS readings 174 are shown as also having a first transient period 186 and a second transient period 188.

In an embodiment, the PRS (e.g., PRS $24_3$) is affixed to the patient (e.g., chest), is disposed in an electromagnetic field produced by the MPS 20, and outputs a signal that is processed by the MPS 20 to produce a series of raw PRS readings 174 over time that indicate the position and/or orientation of the PRS. The SCP filter 168 is configured to process the input series of raw PRS readings, remove relatively small movements, and output a corresponding series of filtered PRS readings—shown in block form in FIG. 1. The filtering action of the SCP filter 168 involves setting the filtered PRS readings to a value equal to the prevailing baseline value (i.e., constant value) while the raw PRS readings 174 stay within a predetermined range of the baseline value. The filtering action removes the motion component contained in the raw PRS readings. The resulting filtered PRS readings make it appear that the PRS is not moving but is rather parked in a stable position corresponding to the assigned constant baseline value. However, the SCP filter 168 is further configured to set the output filtered PRS readings to match the input raw PRS readings 174 unchanged in situations where the raw PRS readings 174—relative to the prevailing baseline value—have reached or even vary to extend outside the predetermined range.

With continued reference to FIG. 5, the first baseline value 176 corresponds to the PRS position relative to a reference position (e.g., an originally registered PRS position/orientation), which may have a stable value of two centimeters. Likewise, the second baseline value 178 may have a stable value of four centimeters, and the third baseline value 180 may have a stable value of zero centimeters. Without loss of generality, the first and second transient periods 176, 178 occur due to first and second C-arm movements of the imaging system (see FIG. 2). In other words, movements of the C-arm result in a change in the position of the PRS within the reference coordinate system. This movement of the PRS device is the type that should be recognized by the system, not filtered out. It should be understood, however, that there are other circumstances that may lead to PRS position changes that should also not be ignored, and indeed should not be filtered but rather recognized (e.g., movement of a procedure table on which the patient rests).

In any event, the SCP filter 168 is also configured to identify PRS position changes of the type that should be recognized not filtered out. The SCP filter 168 accomplished that by monitoring the raw PRS readings for changes in magnitude sufficient to place the raw PRS readings at or outside of the predetermined range surrounding the applicable (prevailing) baseline value. In the illustrated embodiment of FIG. 5, this threshold is set to about one centimeter, in absolute terms, on either side of the baseline. It warrants re-iterating that the baseline value comprises at least one of (i) a baseline position (i.e., one or more components of position, such as an X-axis component, a Y-axis component, a Z-axis component, or any combination thereof), (ii) a baseline orientation (i.e., one or more of pitch orientation angle, a yaw orientation angle, a roll orientation angle, or any combination thereof), or (iii) a baseline position and orientation.

With continued reference to FIG. 5, the SCP filter 168 operates as follows. Initially, a first baseline value (i.e., the first baseline value 176) is defined at a start time. The start time typically can be the start of a medical procedure although the start time can also be the time when the SCP filter 168 is activated by the user. In an embodiment, the main electronic control 12—or the MPS 20 if filtering is implemented therein—can be configured to set the first baseline value 176 after preliminary low pass filtering and/or averaging is performed on the raw PRS readings 174. Once the first baseline value 176 is set, the SCP filter 168 operates to output the filtered PRS readings as made equal to the constant first baseline value (e.g., in the illustrated example of position—at two centimeters), even though the raw PRS readings 174 may indicate small movements of the PRS. This filtering action continues as long as the raw PRS readings 174 stay within the predetermined range 182. The predetermined range 182, in the example of FIG. 5, is set to ±1 cm.

After the start time mentioned above, the SCP filter 168 monitors for, and is configured to detect, the start of a transient period (e.g., first transient period 186), when raw PRS readings 174 change up or down relative to the first baseline value 176 by more than or equal to a threshold amount (i.e., up or down by 1 cm or more). In other words, the first transient period 186 starts when the raw PRS readings 174 vary outside the predetermined range 182. During the first transient period 186, the SCP filter 168 passes the input raw PRS readings 174 unchanged as the output filtered PRS readings 172.

The SCP filter 168 is further configured to determine the end of a transient period, such as the first transient period 186. In an embodiment, this can be recognized when the changes in the raw PRS readings 174 settle down around a new stable/baseline value. Once the end of a transient period has been determined, a new baseline value can be calculated, in an embodiment, by averaging raw PRS data. In the case of C-arm movements causing the transient period, the re-calculation of the new baseline value can be done after the C-Arm movements are completed. An additional mechanism for detecting C-Arm movement may include receiving communication(s) from the fluoroscope imaging system itself (e.g., imaging system 34 shown in FIG. 2). In FIG. 5, the new baseline value is the second baseline value 178.

It should be understood that while the second baseline value 178 is shown as having a value (four centimeters) different from the first baseline value (two centimeters), this is for illustration purposes only. After the SCP filter 168 establishes the second baseline value 178, the SCP filter 168 adopts the second baseline value 178 in outputting the filtered PRS readings 172, provided the raw PRS readings 174 stay within the predetermined range 184 surrounding the second baseline value 178. The operation of the SCP filter 168 described above is an ongoing process, such that additional transient periods can be detected and new, additional baseline values can be established. FIG. 5 shows an additional transient period 188 triggered due to a C-arm movement and the resulting PRS movement that breaches the lower threshold of predetermined range 184. In addition, FIG. 5 shows an additional third baseline value 180 after the second transient period 188.

In sum, during transient periods, for example during the two C-Arm movements in FIG. 5, the SCP filter 168 may pass the raw PRS data to its output wherein the system may compensate for organ and/or imaging equipment motion as described above. However, during the time intervals where baseline value(s) prevail (sub-threshold PRS movements), the SCP filter 168 sets the filtered PRS readings to the constant value associated with the prevailing baseline value. In other words, the SCP filter 168 outputs the constant value so long as the raw PRS readings 174 stay within the predetermined range and thus neither increase nor decrease by more than the predefined thresholds (i.e., in absolute terms, +/−a certain threshold amount). Through these mechanisms, the SCP filter 168 may selectively combat the potentially adverse effects of small skin movements near or at the PRS site by ignoring the small movements contained in the raw PRS readings 174, while allowing PRS movements that should be recognized to pass through.

In addition, during non-transient periods, changes caused by the SCP filter 168 (removing small movements) effectively masks small PRS movements in the filtered PRS readings, and thus downstream motion compensation processing will continue as if the PRS is not moving at all relative to the baseline value (i.e., constant position). The foregoing functionality is effective in keeping the projection/superimposing on track, and operates without attempting to make fine adjustments that are not due to actual organ and/or imaging system movement. In at least one embodiment, any movement may be ignored that is under a threshold movement amount of about 10 millimeters and/or less than 10 degrees and/or was not marked by the "imaging system" as a movement. In another embodiment, the threshold amount may be about 8 millimeters. Alternatively the threshold amount may be an absolute value amount of about 10 millimeters or an absolute value amount of about 8 millimeters.

Figure 6:
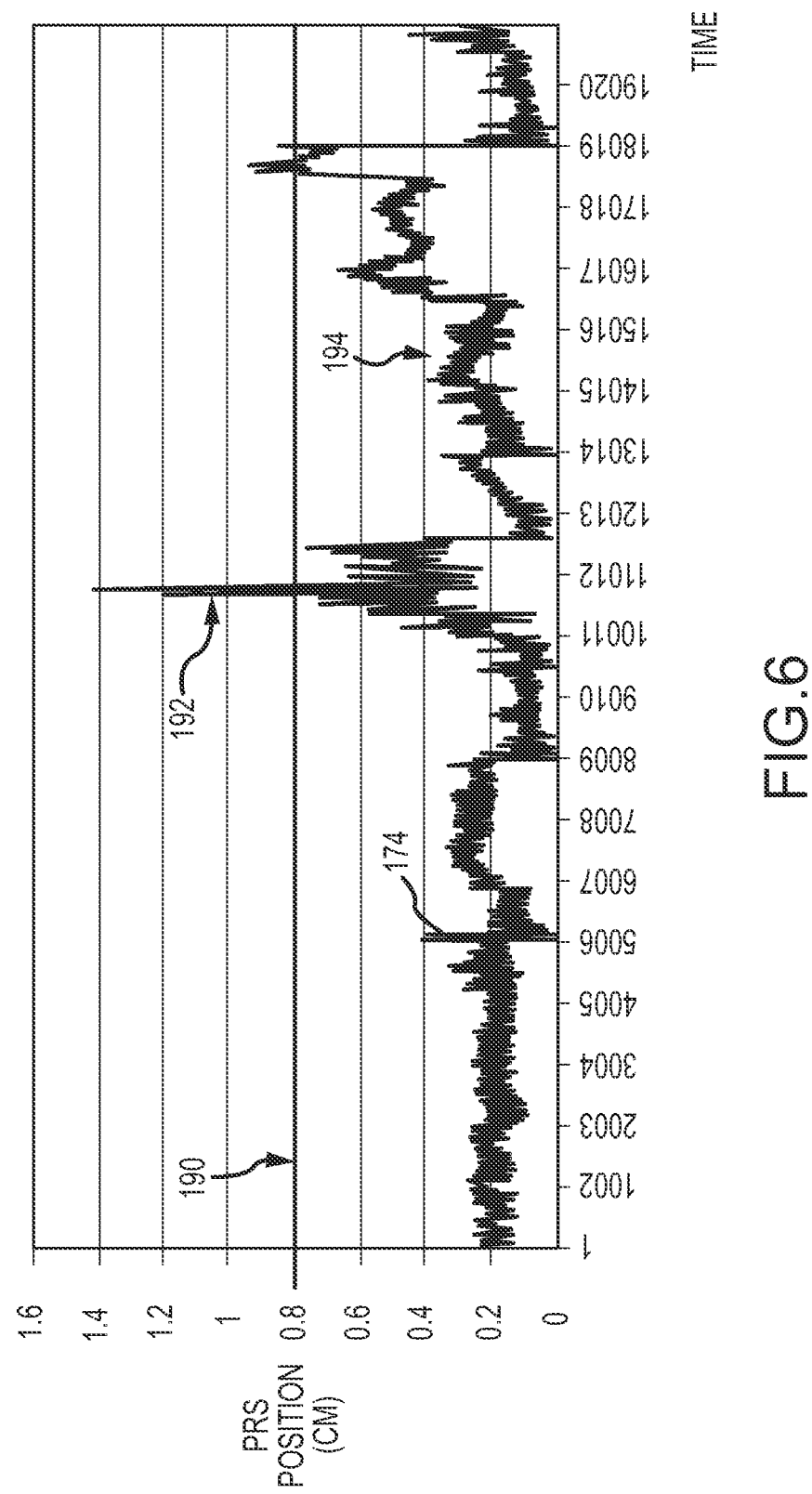
FIG. 6 is a graph of PRS data versus time showing, in an embodiment, a horizontal line representing a threshold amount.

FIG. 6 is a graph of PRS data versus time showing, in an embodiment, a horizontal line representing a threshold amount. In FIG. 6, an upper threshold 190 is set to about 0.8 centimeters for the SCP filter 168, instead of the threshold of about 1.0 centimeters as was the case in the embodiment of FIG. 5. In addition, FIG. 6 shows where the raw PRS readings 174 exceed the threshold 190 (at point 192) and where the raw PRS readings 174 are below the threshold 190 (at point 194).

Figure 7:
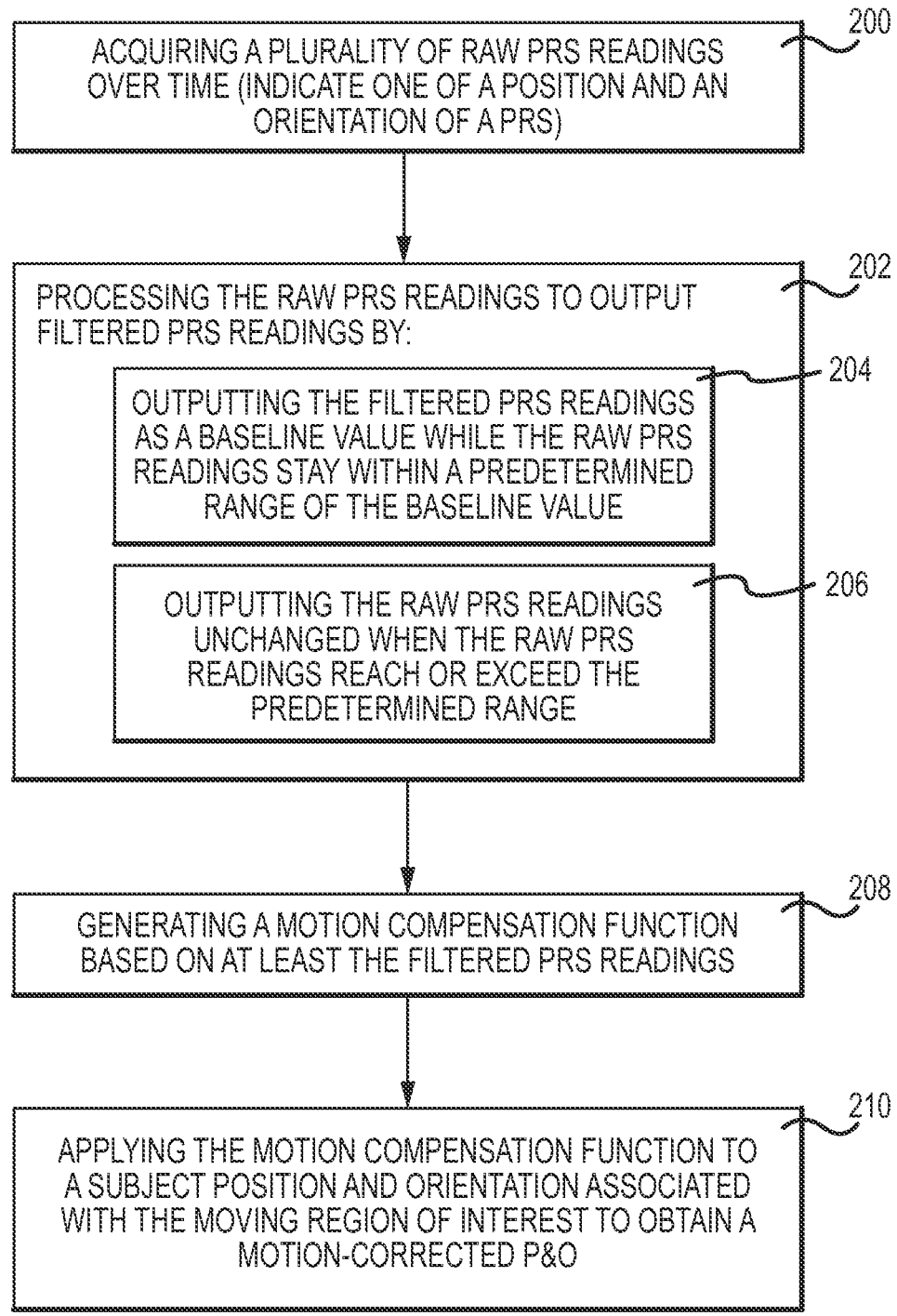
FIG. 7 is a flowchart diagram showing, in an embodiment, a method of motion compensation using at least filtered PRS readings.

FIG. 7 is a flowchart of a method, in an embodiment, of filtering raw PRS readings and using the output filtered PRS readings for motion compensation. Before proceeding, it should be understood that use of the words "first", "second" and so forth are used for description purposes only, but are in no way to be deemed required or limiting. The method includes a number of actions and begins with action 200.

The first action 200 involves acquiring a plurality of raw patient reference sensor (PRS) readings over time where the raw PRS readings indicate at least one of a position and an orientation of a PRS (e.g., PRS $24_3$). The PRS is associated with the moving region of interest.

The second action 202 involves processing the raw PRS readings, using a computer processing apparatus, to output filtered PRS readings. In action 204, such processing may involve outputting the filtered PRS readings as a baseline value while the raw PRS readings are within a predetermined range of the baseline value. In action 206, such processing may further involve outputting the filtered PRS readings to match unchanged the incoming raw PRS readings when the raw PRS readings reach or vary outside of the predetermined range of the baseline value. This action may be performed in accordance with the description set forth hereinabove.

The third action 208 involves generating, using the computer processing apparatus, a motion compensation function based on at least the filtered PRS readings. This may be performed as described hereinabove.

The fourth action 210 involves applying the motion compensation function to a subject position and orientation (P&O) associated with the moving region of interest to obtain a motion-corrected P&O. This action is operative to correct for the motion of the moving region of interest between a first time associated with the subject P&O and a second time associated with the corrected P&O.

While the reference sensor has been described in at least one embodiment as comprising a patient reference sensor (PRS) being used in connection with a display operation, the present disclosure is not so limited. For example, the compensation functions described herein may be useful for many kinds of calculations. Further, the reference sensor may include, but is not limited to, an ECG sensor, a position sensor attached to an invasive medical device (e.g., an internal patient reference sensor), a device configured to generate a heart or cardiac index, and/or a device configured to generate a respiration index. Such reference sensor(s) may work at any time during, before, or after a procedure, and are not limited to when an invasive device, such as a catheter, is in a patient's body. For example, the system can acquire a cine loop prior to inserting a first catheter into the body. Different compensation functions may be implemented independently and/or simultaneously using different indexing data from different reference sensors.

For example, one use may involve superimposing a live anatomical landmark on a cine-loop of a moving region of interest. In this example, the landmark may have a subject P&O associated therewith when the landmark was established at a first time (the first time being capable of being correlated with the moving region of interest). This example may further involve superimposing the landmark at a second time (e.g., the second time corresponding to the timing associated with the particular frame of the cine-loop on which the landmark is to be displayed). The method achieves motion compensation of the subject P&O associated with the landmark so that the landmark can be properly superimposed on the cine-loop (or frame thereof), even during periods of time where the PRS experiences small unintentional movements due to, for example, small skin movements near the PRS or patient head movements, both as already described above.

Experimental Derivation. Analyzing data from various experiments led to the identification of several possible skin/body movements that may affect PRS location when there are no related heart movements. In one such experiment, a test subject laid on a table in a nominal location (such as that shown in FIG. 2) with the PRS on the sternum. Different types of skin and body movements were conducted. Between each movement the patient breathed normally for about 30 seconds, in order to identify each movement. The same test was repeated with and then without an ophthalmic headrest pad/pillow in order to evaluate the data's clinical value. The data from one such test where an ophthalmic pillow may have been used is shown in FIG. 6; a possible threshold amount is shown by the 'horizontal' line about 0.8 centimeters (8 millimeters). The test data was analyzed and compared to live data that was observed with real patients. After optimizing the SCP filter's parameters, it was found that the SCP filter will effectively compensate for any skin movement that is in the range of 0-10 mm and/or that tilts the PRS more than 10 degrees. As described above, larger movements "free the hysteresis" and a new PRS baseline value is thereafter set. New PRS baseline values are set after a low-pass filter/averaging is performed on the new stable position.

Additional Examples. Additional exemplary embodiments of the present disclosure may be summarized by reference to the below outline:

As an initial matter, any physical position and/or orientation (between 1DOF to 6DOF) on the moving organ can be matched to itself although it is not stable in time. This matching can be done by applying a compensation function that interprets any P&O in time to one canonical P&O (the function compensates for the movement in time). Additional important capability is a function that can interpret any P&O in time to itself at a different time. The P&O interpretation function between different times can be implemented using a "compensation function" (sometimes referred to herein as a matching function).

Concerning matching functions, first note that the matching functions can be used even if they are not completely accurate and even if they can operate on a subset of the needed DOF. Secondly, note that the matching functions can use transformation back and forth to a different coordinate system that is less vulnerable to the movements (e.g., an external Patient Reference Sensor or an internal Patient Reference Sensor).

An internal Patient Reference Sensor can improve the accuracy of a determined P&O. In this regard, an internal Patient Reference Sensor is more rigid to the heart (i.e., more closely coupled) as opposed to the external body or to the room's equipment. As described above, the raw external Patient Reference Sensor data can be replaced by filtered external Patient Reference Sensor data. This filtering can reduce skin movements and other movements that are not rigid to the heart.

Concerning matching functions, finally note that the matching functions can use one or more indexed parameters that are available to the system online, and are correlated to the P&O movement. In this case the correlation needs to be "learned" prior to the use of the function; however, the function will be able to interpret historical P&Os from prior times to the learning-period. Such indexed parameters may include: (i) external Patient Reference Sensor and/or respiration belts can be used for extracting a "respiration" index parameter; (ii) an ECG signal can be used for extracting a "heart" index parameter and/or the "respiration" index parameter; and (iii) an internal Patient Reference Sensor can be used for extracting the "heart" index parameter and/or the "respiration" index parameter.

Once one or matching functions have been determined, any operation on several inputs from different times should use the appropriate functions for transferring everything to one state so that they will be consistent. Display of several inputs from different times should use the appropriate functions for transferring such inputs to one consistent state. Concerning display applications, it should be understood that the background image is yet another input that needs to be made consistent with other displays that derive from the sensors. For example: 2D landmark live location on a cine-loop. For another example: 3D "volume mapping" data merge with CT visualization data.

In addition to display-based uses, application of motion compensation to spatial data is also useful. For example, spatial calculations should be conducted so as to be consistent with respect to all inputs (all inputs preferably interpreted to one consistent state). One example of a use with regard to spatial data includes measurement of the length of a vessel from the historical trail of P&Os that where collected by a sensor in that vessel. Another example involves solving the Registration problem of matching the historical location of sensors in a chamber (heart chamber) to the CT chamber shape.

In a further embodiment, an article of manufacture is provided for motion compensation in relation to a moving region of interest in a body. In accordance with such further embodiment, the article of manufacture includes a computer readable non-transitory storage medium having a computer program encoded thereon, where the computer program includes code for performing the methods described hereinbefore. Such embodiments may be configured to execute one or more computer processing apparatuses, multiple computer processing apparatuses that are integrated into a single system or are distributed over and connected together through a communications network, where the network may be wired or wireless.

It should be understood that the system 10, for example main electronic control 12 or a computer processing apparatus in the medical positioning system, or other computing resource available in system 10, as described above, may include conventional processing apparatus known in the art, capable of executing pre-programmed instructions stored in an associated memory, all performing in accordance with the functionality described herein. It is contemplated that the methods described herein, including without limitation the method steps of embodiments of the disclosure, will be programmed in a preferred embodiment, with the resulting software being stored in an associated memory and where so described, may also constitute the means for performing such methods. For example only, the described SCP filter may be implemented in software thus forming means for filtering raw PRS readings and outputting filtered PRS readings, in accord with the instant teachings. Likewise, the described motion compensation function may be implemented in software thus forming means for generating a motion compensation function based on at least the filtered PRS readings. Additionally, the described method(s) for correcting a subject position and orientation using the motion compensation function may be implemented in software thus forming means for correcting a subject position and orientation. Implementation of various features of the disclosure, in software, in view of the foregoing enabling description, would require no more than routine application of programming skills by one of ordinary skill in the art. Such a system may further be of the type having both ROM, RAM, a combination of non-volatile and volatile (modifiable) memory so that the software can be stored and yet allow storage and processing of dynamically produced data and/or signals.

Although numerous embodiments of this disclosure have been described above with a certain degree of particularity, those skilled in the art could make numerous alterations to the disclosed embodiments without departing from the spirit or scope of this disclosure. All directional references (e.g., plus, minus, upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the embodiments. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A method for displaying a moving region of interest located within a body, comprising:

obtaining an image of the moving region of interest within the body at a first time;

acquiring a plurality of raw patient reference sensor (PRS) readings over time where the raw PRS readings indicate at least one of a position and an orientation of a PRS and wherein the PRS is associated with the moving region of interest;

filtering the raw PRS readings and outputting filtered PRS readings by (i) outputting the filtered PRS readings as a baseline value while the raw PRS readings are within a predetermined range of the baseline value; and (ii) outputting the filtered PRS readings as the raw PRS readings when the raw PRS readings reach or vary outside of the predetermined range of the baseline value, wherein said baseline value is determined based on raw PRS readings;

generating, using a computer processing apparatus, a motion compensation function based on at least the filtered PRS readings;

determining, using a positioning system, a subject position and orientation of a medical device at a second time;

correcting, using the computer processing apparatus, the subject position and orientation of the medical device using the motion compensation function that includes a displacement vector which corresponds to the movement of the region of interest between the first time at which the image of the region of interest was acquired and the second time at which the subject position and orientation of the device was determined; and superimposing, using a superimposing processor, a representation of the medical device on the image in accordance with the corrected position and orientation.

2. The method of claim 1, wherein the baseline value comprises a first baseline value wherein said first baseline value comprises at least one of a first baseline position, a first baseline orientation, and a first baseline position and orientation, said filtering further comprising:
establishing the first baseline value at a start time;
detecting, after the start time, the start of a transient period when the raw PRS readings differ from the first baseline value by more than or equal to a threshold amount that defines the predetermined range;
detecting the end of the transient period;
after the start time at which the first baseline value was established and before the start of the transient period, outputting the first baseline value as the filtered PRS readings; and
during the transient period, outputting the raw PRS readings as the filtered PRS readings.

3. The method of claim 2, wherein the threshold amount comprises one of an absolute value of 10 millimeters or less, an absolute value of 10 millimeters, an absolute value of 8 mm or less, and an absolute value of 8 mm.

4. The method of claim 2, wherein the threshold amount comprises an absolute value of 10 degrees or less.

5. The method of claim 2, wherein the threshold amount comprises an absolute value of 10 millimeters and 10 degrees.

6. The method of claim 2, further including:
after the end of the transient period, establishing a second baseline value, and outputting the second baseline value as the filtered PRS readings.

7. The method of claim 6, wherein the first and second baseline values comprise respective constant values.

8. A method for compensating for the motion of a moving region of interest located within a body, comprising:
acquiring a plurality of raw patient reference sensor (PRS) readings over time
where the raw PRS readings indicate at least one of a position and orientation of a PRS that is associated with the moving region of interest;
processing the raw PRS readings, using a computer processing apparatus, to output filtered PRS readings, wherein the processing includes:
(i) outputting the filtered PRS readings as a baseline value while the raw PRS readings are within a predetermined range of the baseline value;
(ii) outputting the filtered PRS readings as the raw PRS readings when the raw PRS readings reach or vary outside of the predetermined range of the baseline value, wherein said baseline value is determined based on raw PRS readings;
generating, using the computer processing apparatus, a motion compensation function based on at least the filtered PRS readings; and
applying the motion compensation function including a displacement vector to a subject position and orientation (P&O) associated with the moving region of interest to obtain a motion corrected P&O, wherein the displacement vector corresponds to the movement of the moving region of interest between a first time associated with the subject P&O and a second time associated with the corrected P&O.

9. The method of claim 8, wherein the subject P&O and the motion corrected P&O both refer to the same anatomical point in the moving region of interest at the first time and at the second time, respectively.

10. The method of claim 8, wherein the motion compensation function is used for displaying a medical device on a prerecorded image of the moving region of interest.

11. The method of claim 8, wherein the PRS comprises one of a position sensor attached to an invasive medical device, a position sensor attached to an exterior of the body, an ECG monitor configured to produce an ECG signal, a device configured to generate a heart index, and a device configured to generate a respiration index.

12. The method of claim 8 wherein the subject P&O comprises an historical P&O obtained prior to said acquiring, processing, and generating of the motion compensation function.

13. The method of claim 8 wherein the subject P&O is associated with an anatomical landmark to be superimposed on a cine-loop indicating an anatomical point in the moving region of interest, and wherein the second time is selected in accordance with the timing of the cine-loop being displayed.

14. The method of claim 8 wherein the subject P&O comprises a plurality of subject P&Os associated with a path through a vessel in the body, wherein the corrected P&O comprises a corresponding plurality of corrected P&Os.

15. The method of claim 8, wherein the baseline value comprises a first baseline value, the first baseline value comprising at least one of a first baseline position, a first baseline orientation, and a first baseline position and orientation, said method further comprising:
establishing the first baseline value at a start time;
detecting, after the start time, the start of a transient period when the raw PRS readings differ from the first baseline value by more than or equal to a threshold amount that defines the predetermined range;
detecting the end of the transient period.

16. The method of claim 15, wherein the threshold amount comprises one of an absolute value of 10 millimeters or less, an absolute value of 10 millimeters, an absolute value of 8 mm or less, and an absolute value of 8 mm.

17. The method of claim 15, wherein the threshold amount comprises an absolute value of 10 degrees or less.

18. The method of claim 15, wherein the threshold amount comprises an absolute value of 10 millimeters and 10 degrees.

19. An apparatus for compensating for the motion of a moving region of interest located within a body, comprising:
a medical positioning system and a patient reference sensor (PRS) configured to be associated with the moving region of interest, said positioning system being configured to acquire a series of raw PRS readings indicative of at least one of a position and an orientation of said PRS over time;
means for filtering said raw PRS readings and outputting filtered PRS readings, said filtering means being configured to:
output filtered PRS readings as a baseline value while said raw PRS readings are within a predetermined range of said baseline value; and
output filtered PRS readings as the raw PRS readings when said raw PRS readings reach or vary outside of said predetermined range of the baseline value, wherein said baseline value is determined based on raw PRS readings;
means for generating a motion compensation function based on at least said filtered PRS readings; and
means for correcting a subject position and orientation using said motion compensation function that includes a displacement vector which corresponds to the movement of the region of interest between a current time at which said subject position and orientation is being corrected and an earlier time.

20. The apparatus of claim 19, wherein the baseline value comprises a first baseline value, said first baseline value comprising at least one of a first baseline position, a first baseline orientation, and a first baseline position and orientation, said filtering means being further configured to:
- establish said first baseline value at a start time;
- detect a start of a transient period when said raw PRS readings differ from said first baseline value by more than or equal to a threshold amount that defines said predetermined range;
- detect an end of said transient period;
- establish a second baseline value; and
- output filtered PRS readings as said second baseline value while said raw PRS readings are within said predetermined range of said second baseline value.

* * * * *